(12) United States Patent
Chen

(10) Patent No.: US 12,147,055 B2
(45) Date of Patent: Nov. 19, 2024

(54) HEAD-MOUNTED FIXING DEVICE

(71) Applicant: E-LEAD ELECTRONIC CO., LTD., Changhua (TW)

(72) Inventor: Stephen Chen, Changhua (TW)

(*) Notice: Subject to any disclaimer, the term of this patent is extended or adjusted under 35 U.S.C. 154(b) by 322 days.

(21) Appl. No.: 17/574,510

(22) Filed: Jan. 12, 2022

(65) Prior Publication Data
US 2023/0040478 A1 Feb. 9, 2023

(30) Foreign Application Priority Data

Aug. 4, 2021 (TW) .................................. 110209156
Nov. 22, 2021 (TW) .................................. 110213790

(51) Int. Cl.
*G02B 27/02* (2006.01)
*G02B 7/182* (2021.01)
*G02B 17/06* (2006.01)

(52) U.S. Cl.
CPC .......... *G02B 27/028* (2013.01); *G02B 7/1822* (2013.01); *G02B 17/0621* (2013.01); *G02B 27/027* (2013.01)

(58) Field of Classification Search
CPC .. G02B 27/028; G02B 27/027; G02B 7/1822; G02B 17/0621
USPC .......................................................... 359/815
See application file for complete search history.

(56) References Cited

U.S. PATENT DOCUMENTS

2021/0302749 A1* 9/2021 Law .................... G02B 27/0176

FOREIGN PATENT DOCUMENTS

CN 207232521 U * 4/2018
TW I677709 B 11/2019

* cited by examiner

*Primary Examiner* — Wyatt A Stoffa
*Assistant Examiner* — Mitchell T Oestreich
(74) *Attorney, Agent, or Firm* — Bruce Stone LLP; Joseph A. Bruce

(57) ABSTRACT

A head-mounted fixing device includes: a head frame including two side frame portions, and a front frame portion located between the two side frame portions and connected to the two side frame portions, and the two side frame portions and the front frame portion being made of rigid materials; an elastic piece including one end connected to the front frame portion; a headgear including an arc portion and a top portion, wherein two ends of the arc portion are respectively connected to the two side frame portions, one end of the top portion is connected to another end of the elastic piece, and another end of the top portion is connected to the arc portion; it is characterized in that the front frame portion is used to abut against a user's forehead to provide a fulcrum.

16 Claims, 10 Drawing Sheets

HEAD-MOUNTED FIXING DEVICE

BACKGROUND

Field of the Invention

The present invention relates to a fixing device, and more particularly to a head-mounted fixing device.

Description of Related Art

The present medical science has proved that 5% of the causes of myopia are genetic factors. Other causes of myopia are mostly caused by long-term close viewing. The main activities of long-term close viewing are reading and writing. With the progress of civilization, the time spent viewing mobile phones, tablets and computers has increased significantly in recent years, and human myopia has gradually become normal.

Normally, myopia is the result of the increase in the length of the eyeball, the eyeball changes from a round shape to an oval shape. When looking at a distant scene, the crystalline lens can no longer change its shape through adjustment, so that the image cannot be correctly projected on the retina. Especially children's lens is still in the developmental stage, and it is more likely to change shape due to excessive eye use. From the foregoing, how to limit the distance of objects not too close to the eyes has become an important issue for modern people.

Please refer to Taiwan Patent Publication No. 1677709, which disclosed a display device assembly, which essentially comprises a frame, an optical element and an auxiliary component, and allows a display unit (such as a mobile phone), in particular, the optical element in this patent, to be placed on the frame and located on the transmission path of the image beam of the display unit. Since the optical element is a concave lens with a multilayer coating, the image beam provided by the display unit can be transmitted to the optical element is reflected into the user's eyes by the multilayer coating on the optical element, so that the user can view the optical element in the viewing direction, and obtain a virtual image when viewing the optical element, thereby allowing the virtual image is combined with the environmental image presented in the real world. However, the design of this display device has the problem of instability in wearing.

SUMMARY

One objective of the present invention is to provide a head-mounted fixing device which can be worn firmly.

A head-mounted fixing device comprises:
a head frame including two side frame portions, and a front frame portion located between the two side frame portions and connected to the two side frame portions, and the two side frame portions and the front frame portion being made of rigid materials;
a headgear including an arc portion and a top portion, wherein two ends of the arc portion are respectively connected to the two side frame portions, one end of the top portion is connected to the front frame portion, and another end of the top portion is connected to the arc portion; it is characterized in that the front frame portion is used to abut against a user's forehead to provide a fulcrum, the top portion supports the fulcrum, the arc portion is used to surround and abut against the back of the user's head, and the two side frame portions are used as levers, so that the arc portion prevents the head-mounted fixing device from falling forward.

In a preferred embodiment, an insertion hole is defined at one end of each of the two side frame portions, the arc portion is a headband, two ends of the arc portion are inserted through the two insertion holes, respectively, and are fixed to the arc portions by hook and loop fasteners, so that the arc portion is connected to the two side frame portions.

In a preferred embodiment, the top portion includes an elastic piece, one end of the elastic piece is connected to the front frame portion, and another end of the elastic piece is connected to the arc portion. Alternatively, in another preferred embodiment, the top portion includes an elastic piece and a support strap, one end of the elastic piece is connected to the front frame portion, another end of the elastic piece is connected to one end of the support strap, and another end of the support strap is connected to the arc portion.

In a preferred embodiment, the elastic piece includes at least one stretchable structure.

In a preferred embodiment, the top portion includes an elastic piece and a support strap, one end of the elastic piece is connected to the front frame portion, another end of the elastic piece is connected to one end of the support strap and is provided with a through hole, another end of the support strap is connected to the arc portion, and the end of the support strap connected to the elastic piece is inserted through the through hole and then stick to the support strap through a hook and loop fastener so that the support strap is connected to the elastic piece.

In a preferred embodiment, the top portion includes an elastic piece, one end of the elastic piece is connected to the front frame portion and is provided with two through holes for the arc portion to pass through, and another end of the elastic piece is connected to the arc portion.

In a preferred embodiment, the head-mounted fixing device further includes:
an arm assembly connected to the head frame;
a reflection assembly mounted on the arm assembly and including a reflection sheet for reflecting a projected image; and
a magnifying assembly connected to the arm assembly so that the reflection assembly is located between the magnifying assembly and the user's head, and the magnifying assembly includes a magnifying sheet for receiving, magnifying and projecting the projected image to the user's eyes. Optionally, the reflection sheet is a convex mirror, and the magnifying sheet is a concave mirror.

In a preferred embodiment, the two side frame portions are pivotally connected to the front frame portion, and a first pivot is provided at each pivoting connection between each of the two side frame portions and the front frame portion.

In a preferred embodiment, the head-mounted fixing device further comprises two counterweight elements, which are disposed on two sides of the arc portion.

In a preferred embodiment, a second pivot is provided at each pivoting connection between the arm assembly and at least one of the magnifying assembly and the reflection assembly.

With the virtual image imaging principle of the concave mirror, the object is magnified several times and imaged at a distance farther than the actual object distance. This optical technology is used to solve the problem of the user looking at close objects for a long time, which not only allows the user's eyes to see the object from a distance of one meter away, but also magnifies the object so that the user can see clearly.

DETAILED DESCRIPTION

Figure 1:
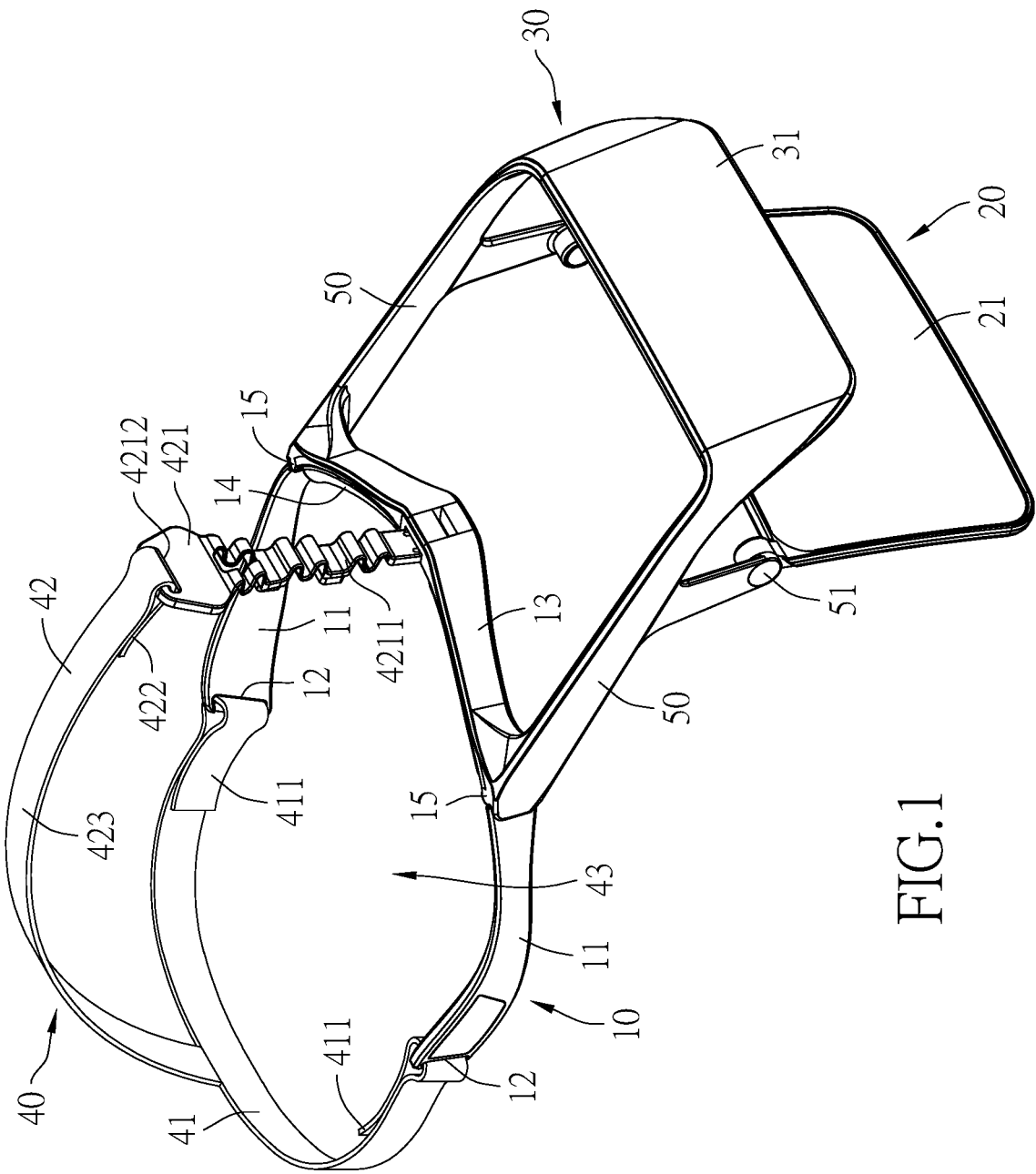
FIG. 1 is a three-dimensional view of the invention in a first embodiment.
Figure 2:
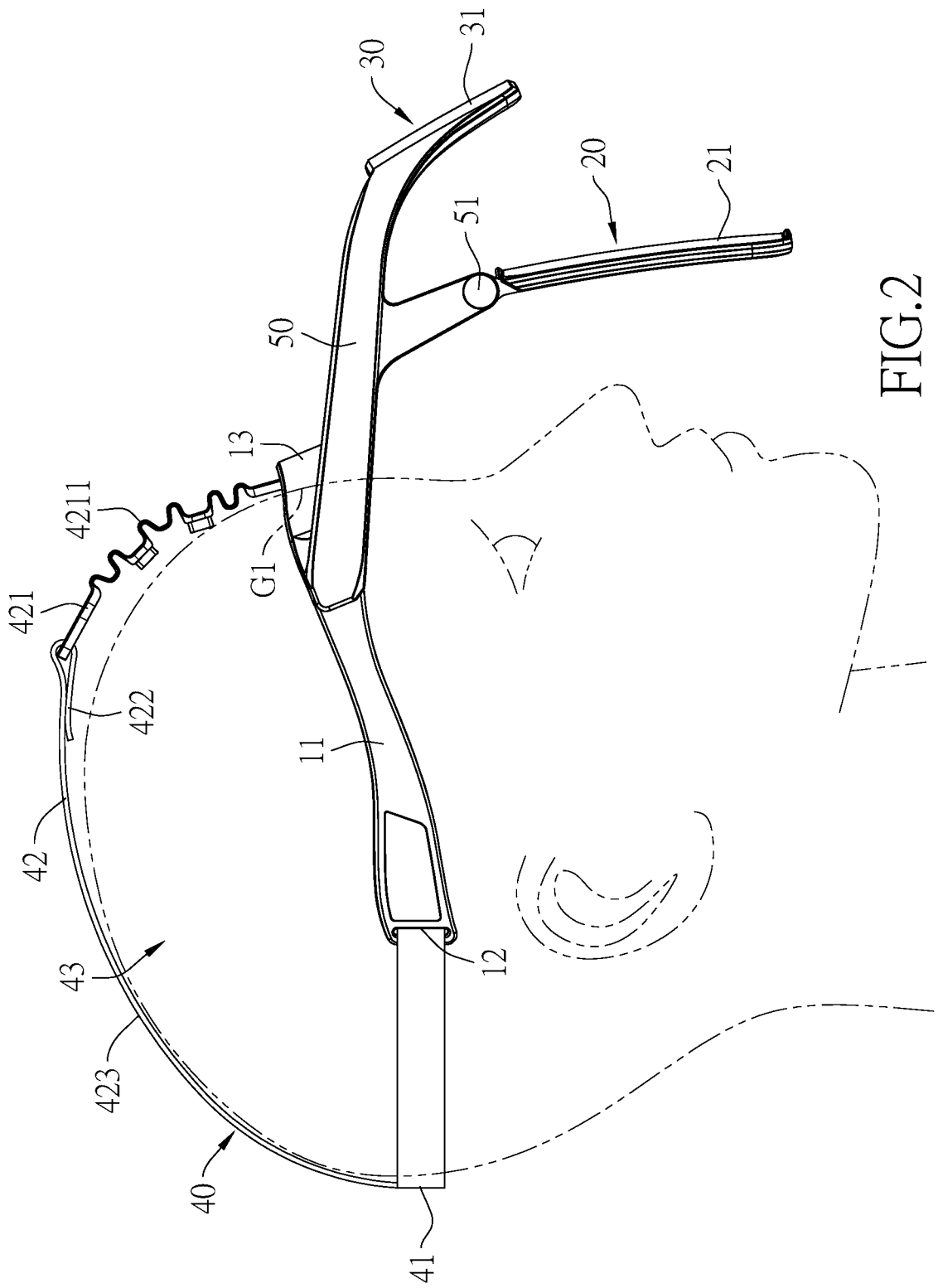
FIG. 2 is a side view of the invention in the first embodiment.
Figure 3:
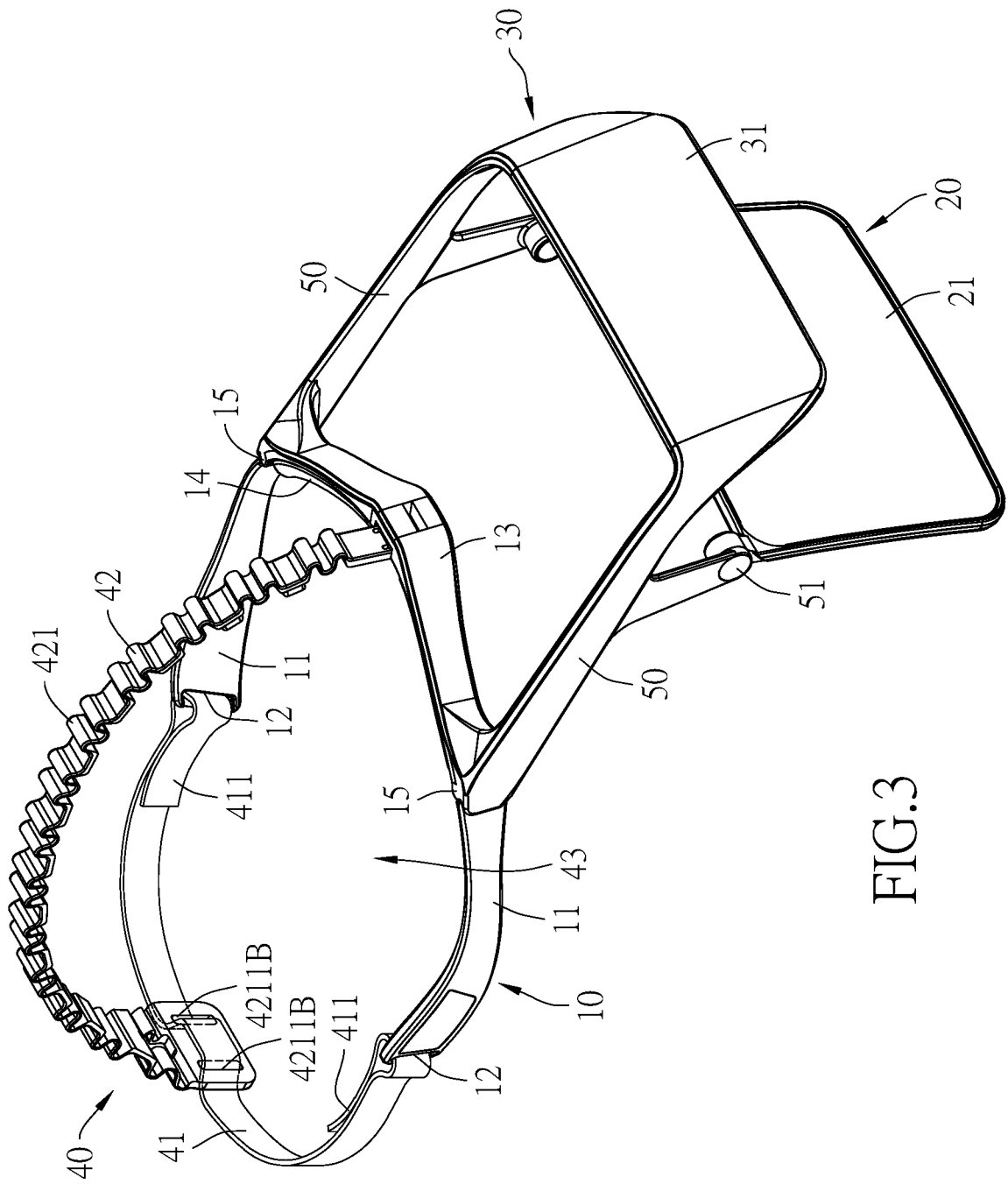
FIG. 3 is a perspective view of the invention in a second embodiment.

Please refer to FIGS. 1 and 2, the present invention is a head-mounted fixing device, which essentially comprises: an arm assembly 50, a head frame 10, a reflection assembly 20, a magnifying assembly 30 and a headgear 40.

The head frame 10 includes two side frame portions 11, and a front frame portion 13 located between the two side frame portions 11 and connected to the two side frame portions 11. The two side frame portions 11 are used to abut against two opposite lateral sides of a user's head, the front frame portion 13 is used to abut against the user's forehead, and the two side frame portions 11 and the front frame portion 13 are made of rigid materials. In this embodiment, the two side frames portions 11 are respectively pivotally connected to two opposite ends of the front frame portion 13, and a first pivot 15 is provided at each pivoting connection between each front end of the two side frame portions 11 and the front frame portion 13; however, the present invention is not limited to this pivoting connection manner. Therefore, when not in use, the two side frame portions 11 can be folded by pivoting the first pivots 15. In this embodiment or other embodiments, a pad 14 is provided on a surface of the front frame portion 13 facing the user's head. The pad 14 is used to abut against the forehead to improve wearing comfort. An insertion hole 12 is defined at one end of each of the two side frame portions 11.

The arm assembly 50 is connected to the head frame 10.

The reflection assembly 20 is mounted on the arm assembly 50, and the reflection assembly 20 includes a reflection sheet 21 for reflecting a projected image; in this embodiment, the reflection assembly 20 reflects the projected image toward the front of the user's head. The reflection sheet 21 is, for example, a convex mirror.

The magnifying assembly 30 is connected to the arm assembly 50 so that the reflection assembly 20 is located between the magnifying assembly 30 and the user's head, and the magnifying assembly 30 includes a magnifying sheet 31 for receiving, magnifying and projecting the projected image to the user's eyes. In this embodiment, the imaging principle of the magnifying sheet 31 is imaging through a concave mirror, so that the virtual image in the magnifying sheet 31 can be magnified and the distance of the virtual image to the user's eyes can be further increased. Specifically, the magnifying sheet 31 is, for example, a concave mirror. As shown in FIG. 5, the arm assembly 50 and the magnifying assembly 30 are pivotally connected through a first pivot group 51, so that the inclination angle of the magnifying assembly 30 can be adjusted. However, the present invention is not limited to this pivotal connection. Please refer to FIG. 4, the first pivot group 51 can also be arranged between the arm assembly 50 and the reflection assembly 20, so that an inclination angle of the reflection assembly 20 is adjustable.

An elastic piece 421 includes a first end connected to the front frame portion 13. The elastic piece 421 is used to abut against the top of the user's head so that the elastic piece 421 bends and abuts against the top of the users' head. The elastic piece 421 includes at least one stretchable structure 4211, which can be, for example, but not limited to, a wave structure and is made of elastic material, so it can be stretched, compressed and bent.

The headgear 40 includes an arc portion 41 and a top portion 42. Two ends of the arc portion 41 are respectively connected to the arm assembly 50, one end of the top portion 42 is connected to the arm assembly 50, and the other end of the top portion 42 is connected to the arc portion 41, so that the arc portion 41, the top portion 42 and the arm assembly 50 jointly form a wearing space 43. In a first embodiment, the arc portion 41 is a headband, and two ends of the arc portion 41 are inserted through the two insertion holes 12, respectively, and then two hook and loop fasteners 411 are respectively provided at two ends of the arc portion 41 and folded back and fixed to the arc portion 41. Besides, the arc portion 41 and the hook and loop fasteners 411 can work with each other to adjust the length of the arc portion 41. It is characterized in that the front frame portion 13 is used to abut against the user's forehead to provide a fulcrum G1. The elastic piece 421 supports the fulcrum G1 with its elastic force so that the front frame portion 13 will not slide down, the arc portion 41 is used to surround and abut against the back of the user's head, and the two side frame portions 11 are used as levers, so that the arc portion 41 prevents the head-mounted fixing device from falling forward.

Please refer to FIGS. 1 and 2, in the first embodiment, the top portion 42 includes the elastic piece 421 and a support strap 423, one end of the elastic piece 421 connected to the support strap 423 is provided with a through hole 4212, and one end of the support strap 423 connected to the elastic piece 421 is inserted through the through hole 4212 and then stick to the support strap 423 through a hook and loop fastener 422 to connect the support strap 423 to the elastic piece 421, and the support strap 423 and the hook and loop fasteners 422 can cooperate with each other to adjust the length of the top portion 42. In a second embodiment, the top portion 42 is only composed of the elastic piece 421, one end of the elastic piece 421 is connected to the front frame portion 13 of the head frame 10, and the other end of the elastic piece 421 is provided with two through holes 4211B, and two through holes 4211B are provided for the arc portion 41 to pass through.

Figure 4:
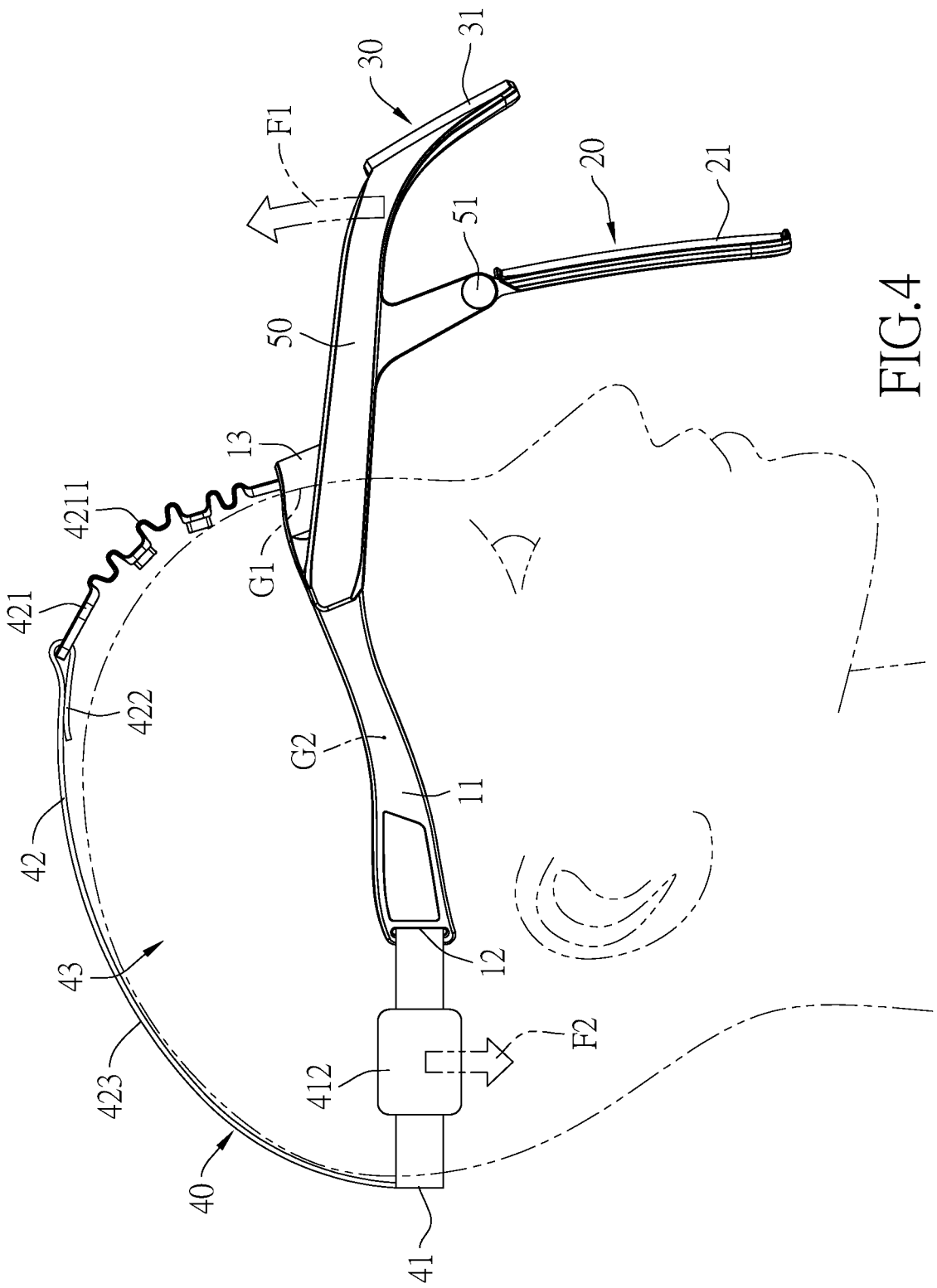
FIG. 4 is a side view of the invention in a third embodiment.
Figure 5:
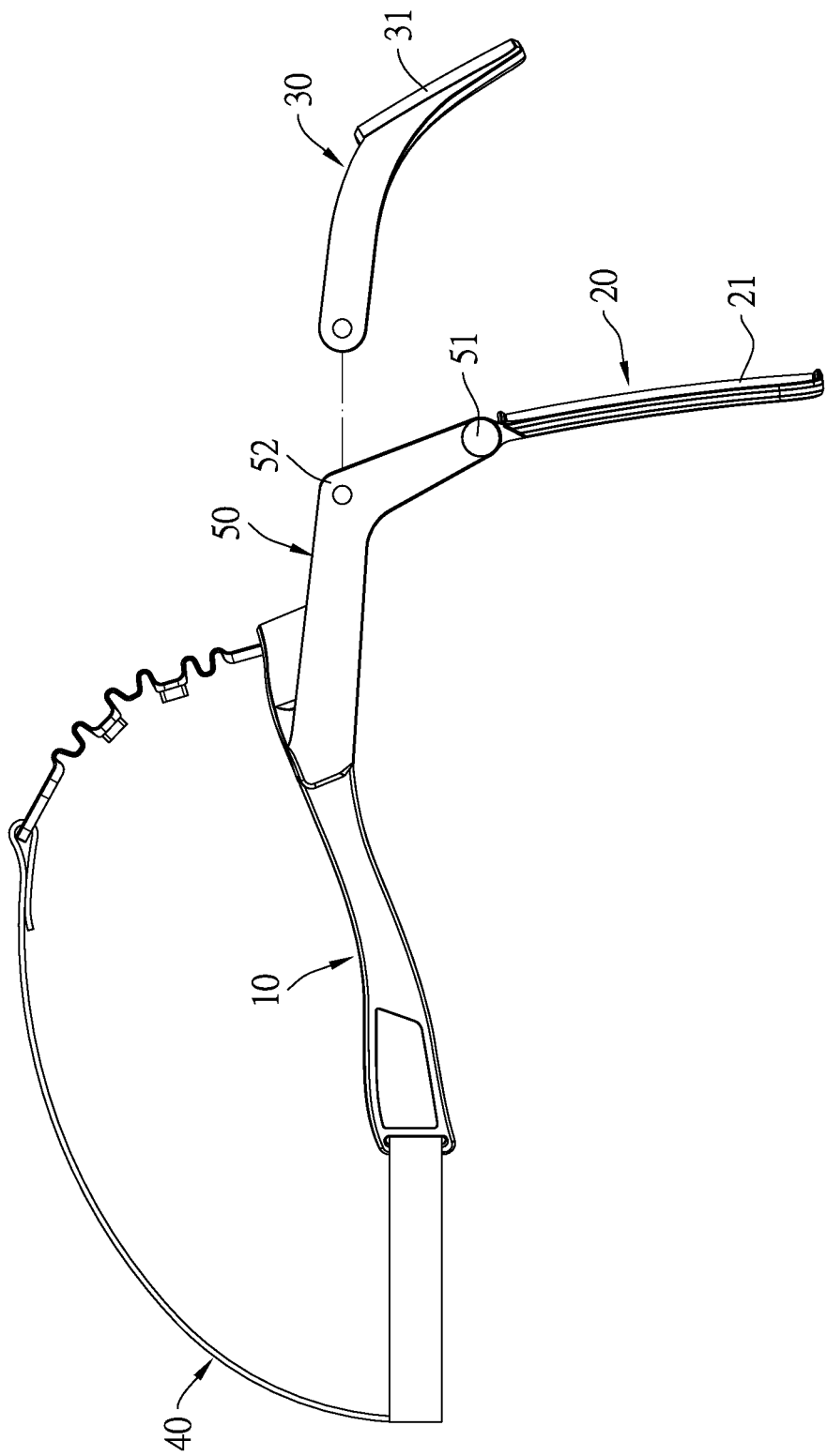
FIG. 5 is a side view of the invention in a fourth embodiment.

Please refer to FIG. 4, a third embodiment of the invention further includes: two counterweight elements 412, which are disposed on two sides of the arc portion 41, and the two side frame portions 11 are abutted against the two opposite sides of the user's head to provide two fulcrums G2. By using the principle of leverage, with the two fulcrums G2 as the center, the two counterweight elements 412 produce downward forces F2, consequently the arm assembly 50 generates an upward force F1 to prevent the reflection assembly 20 and the magnifying assembly 30 from sagging, so that the arc portion 41 does not need to tighten the user's head, which improves the comfort during use.

Figure 6:
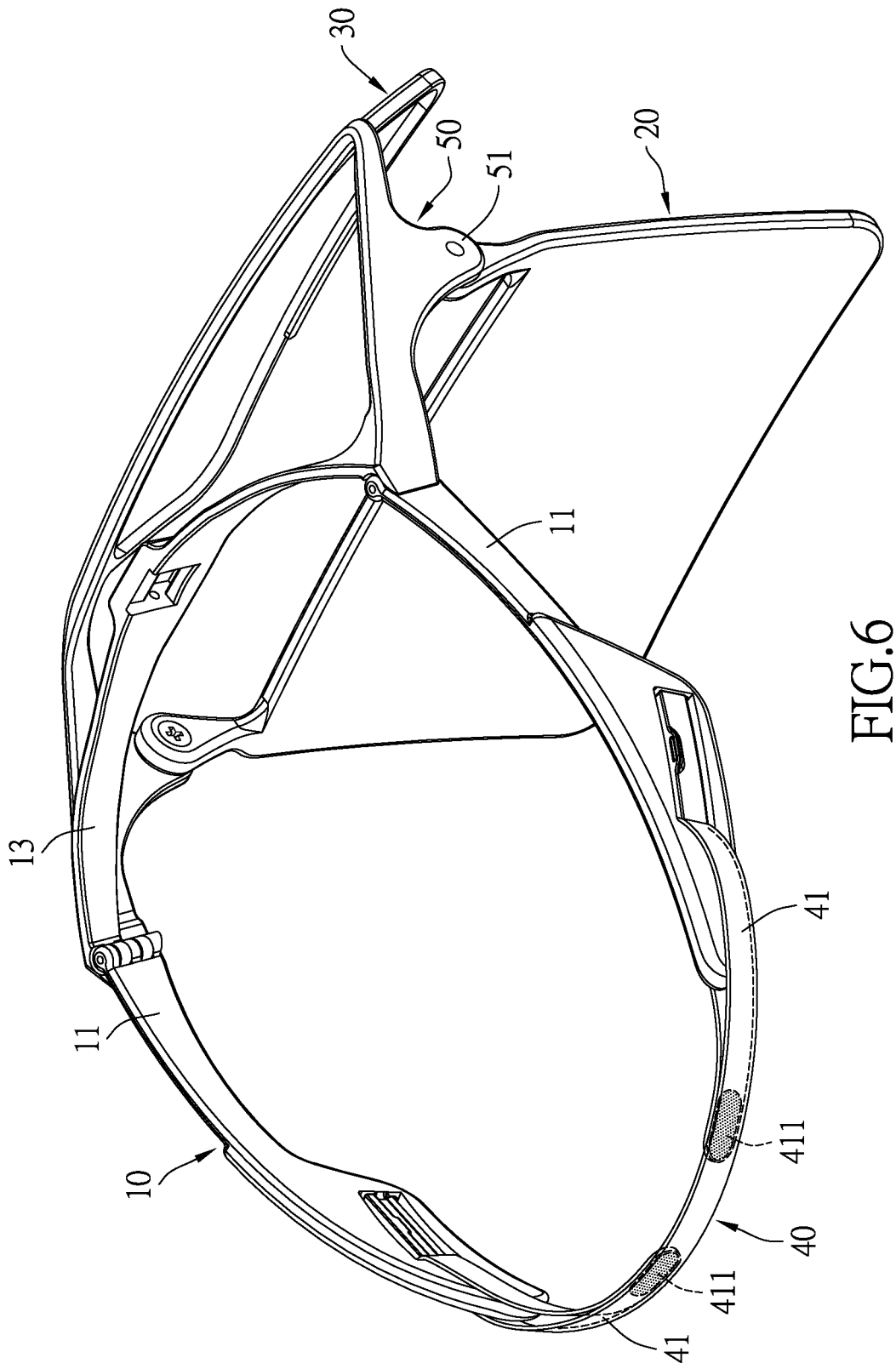
FIG. 6 is a three-dimensional view of the invention in a fifth embodiment.
Figure 7:
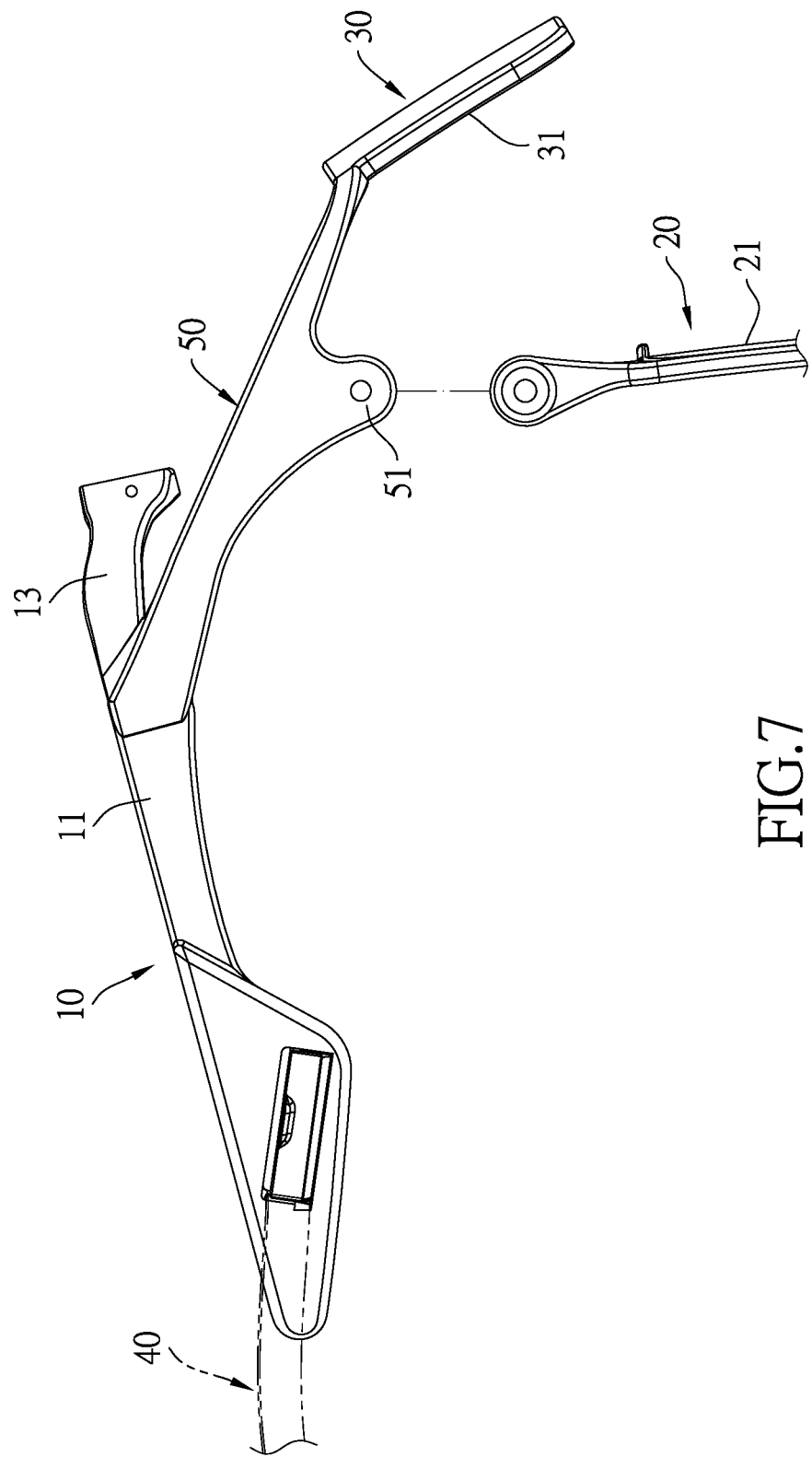
FIG. 7 is an exploded side view of the invention in the fifth embodiment.

Referring to FIGS. 6 and 7, the headgear 40 includes an arc-shaped front frame portion 13, and two arc-shaped side frame portions 11 connected to two ends of the front frame portion 13 respectively. The front frame portion 13 is provided for abutting against a user's forehead, the two side frame portions 11 are provided for clamping on two opposite lateral sides of the user's head. The arm assembly 50 is U-shaped and includes two opposite ends which are respectively connected to the portions of the front frame portion 13 that are connected to the two side frame portions 11, so that the arm assembly 50 extends toward the front of the user's head. The arm assembly 50 includes a first pivot group 51. The reflection assembly 20 reflects the projected image toward the front of the user's head. The imaging principle of the magnifying sheet 31 is imaging through a concave mirror, and the imaging formula of the magnifying sheet 31 is:

$$1/p + 1/q = 1/f$$

(p: image distance, q: object distance, f: focal length)

Through the foregoing formula, not only the virtual image in the magnifying sheet 31 can be enlarged, but the distance of the virtual image can be increased.

In a fifth embodiment, the angle of the magnifying assembly 30 is fixed, and the reflection assembly 20 can only be adjusted through the first pivot group 51 to adjust the imaging position of the virtual image in the magnifying sheet 31.

Furthermore, the headgear 40 is respectively provided with two hook and loop fasteners 411 and an arc portion 41. As shown in FIG. 6, the headgear 40 is a belt, the two ends of the headgear 40 inserted through the ends of the side frame portions 11 are respectively provided with the hook and loop fastener 411, and the middle portion of the headgear 40 is provided with the arc portion 41 which can be bonded to or torn apart from the corresponding hook and loop fasteners 411 to change the bonding position to adjust the size of the headgear 40. However, the structure for adjusting the size of the headgear 40 is not the main feature of this invention, and there are still various implementations. For instance, one end of the hook and loop fasteners 411 can be fixedly connected to one of the side frame portions 11, and one end of the arc portion 41 can be fixedly connected to the other side frame portion 11 to achieve the function of adjusting the size of the headgear 40. Alternatively, the headgear 40 may be two belts fixed to the side frame portions 11, one end of one of the belts is provided with an annular buckle element for insertion of the end of the other belt, so as to form an adjustable positioning structure. Or, an engaging device consisting of a row of holes and one male buckle element is provided at the ends of the two belts to buckle in different holes with the male buckle element. The size of the headgear 40 can also be adjusted through the annular buckle element or the engaging device.

Figure 8:
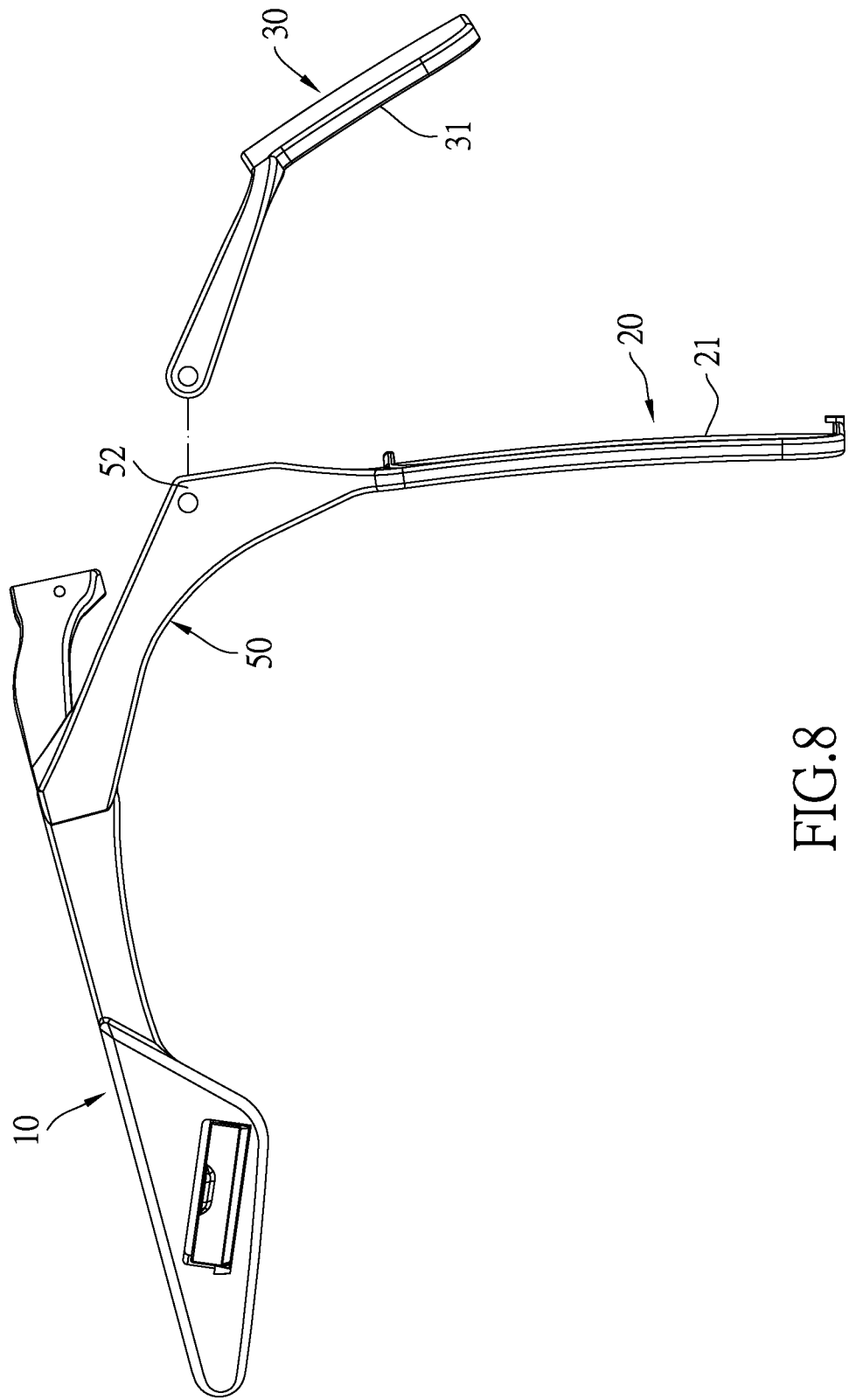
FIG. 8 is an exploded side view of the invention in a sixth embodiment.

Please refer to FIG. 8, in a sixth embodiment, the arm assembly includes a second pivot group 52, and the magnifying sheet 31 is disposed on the second pivot group 52, so that, when the second pivot group 52 pivots, the angle of the magnifying sheet 31 can be adjusted.

Figure 9:
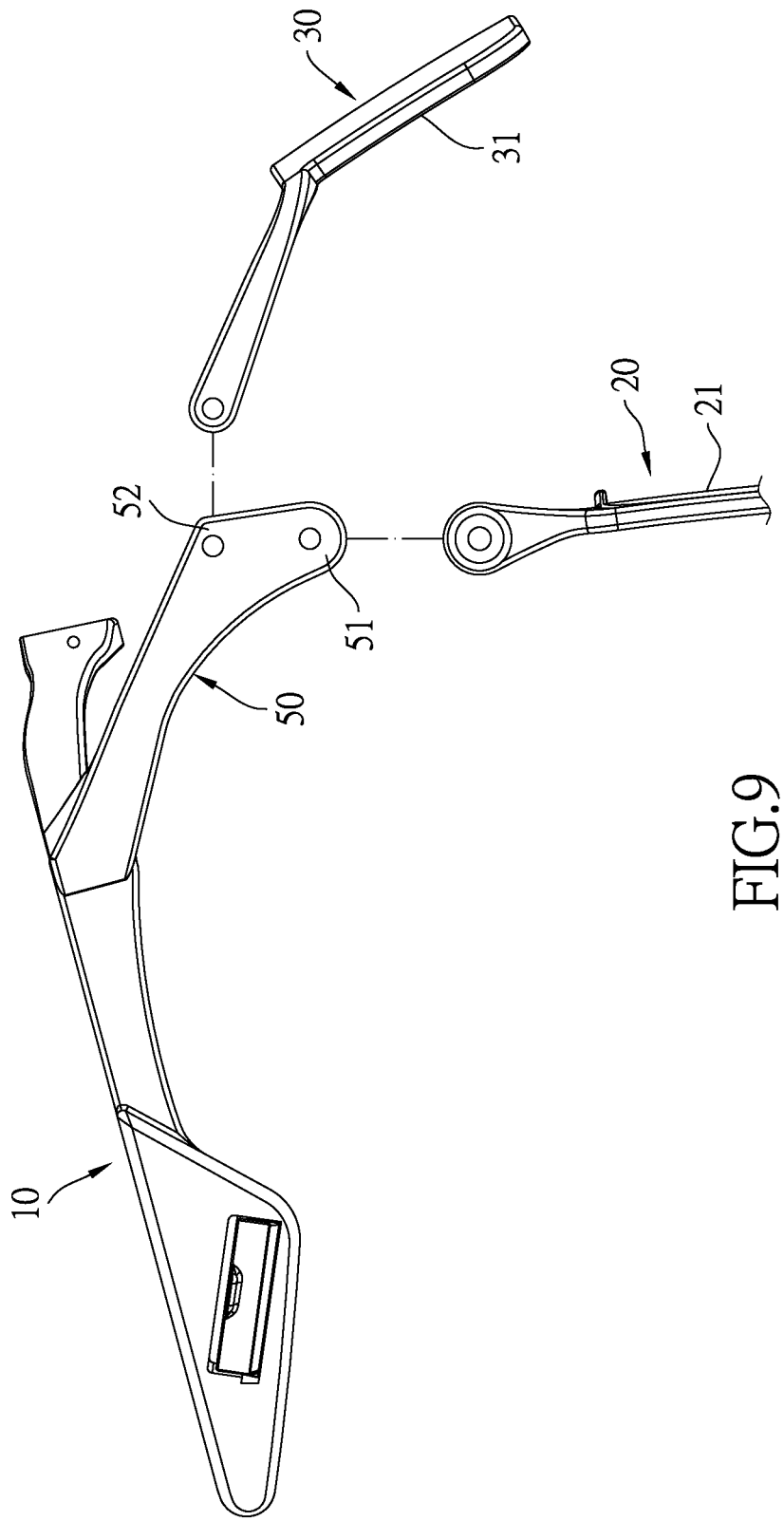
FIG. 9 is a side exploded view of the invention in a seventh embodiment.

Please refer to FIG. 9, in the seventh embodiment, the arm assembly 50 includes a first pivot group 51 and a second pivot group 52, the reflection sheet 21 is disposed on the first pivot group 51, and the magnifying sheet 31 is arranged on the second pivot group 52, so that the angles of the reflection sheet 21 and the magnifying sheet 31 can both be adjusted.

Figure 10:
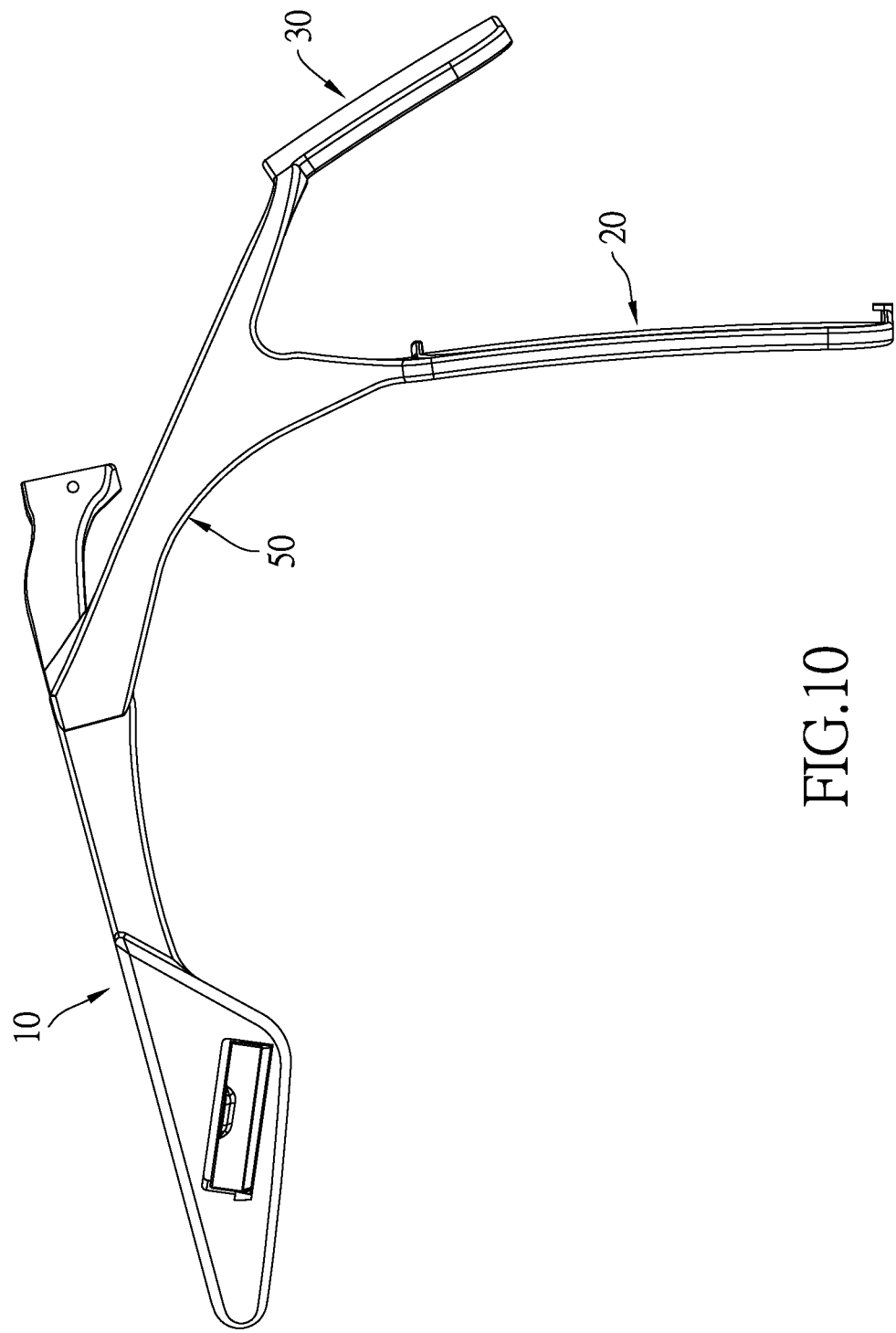
FIG. 10 is a side exploded view of the invention in an eighth embodiment.

Referring to FIG. 10, in A eighth embodiment, the first pivot group 51 and the second pivot group 52 are not used, the reflection sheet 21 and the magnifying sheet 31 are fixedly connected to the headgear 40, so that the angles of the reflection sheet 21 and the magnifying sheet 31 are unadjustable.

The above is the structural configuration and connection relationship of the invention in a preferred embodiment. The use of the present invention and the effects it can produce are as follows:

After the user puts head into the wearing space 43, the user's line of sight will face the magnifying assembly 30, and the image in front of the user's line of sight uses the virtual image imaging principle of the concave mirror in physical optics to magnify the object several times and image it at a distance farther than the actual object distance. This optical technology is used to solve the problem of the user looking at close objects for a long time, which not only allows the user's eyes to see the object from a distance of one meter away, but also magnifies the object so that the user can see clearly.

Please refer to FIG. 5, after the user wears the headgear 40, the user's line of sight will face the magnifying assembly 30, and the image in front of the user's line of sight uses the virtual image imaging principle of the concave mirror in physical optics to magnify the object several times and image it at a distance farther than the actual object distance. This optical technology is used to solve the problem of the user looking at close objects for a long time, which not only allows the user's eyes to see the object from a distance of one meter away, but also magnifies the object so that the user can see clearly.

What is claimed is:

1. A head-mounted fixing device comprising:
    a head frame including two side frame portions, and a front frame portion located between the two side frame portions and connected to the two side frame portions, and the two side frame portions and the front frame portion being made of rigid materials;
    a headgear including an arc portion and a top portion, wherein two ends of the arc portion are respectively connected to the two side frame portions, one end of the top portion is connected to the front frame portion, and another end of the top portion is connected to the arc portion;
    wherein the front frame portion is used to abut against a user's forehead to provide a fulcrum, the top portion supports the fulcrum, and the arc portion is used to surround and abut against the back of the user's head; and the two side frame portions are pivotally connected to the front frame portion, and a first pivot is provided at each pivoting connection between each of the two side frame portions and the front frame portion.

2. The head-mounted fixing device as claimed in claim 1, wherein an insertion hole is defined at one end of each of the two side frame portions, the arc portion is a headband, two ends of the arc portion are inserted through the two insertion holes, respectively, and are fixed to the arc portions by hook and loop fasteners, so that the arc portion is connected to the two side frame portions.

3. The head-mounted fixing device as claimed in claim 1 further comprising two counterweight elements, which are disposed on two sides of the arc portion.

4. The head-mounted fixing device as claimed in claim 1 further comprising:
an arm assembly connected to the head frame;
a reflection assembly mounted on the arm assembly and including a reflection sheet for reflecting a projected image; and
a magnifying assembly connected to the arm assembly so that the reflection assembly is located between the magnifying assembly and the user's head, and the magnifying assembly includes a magnifying sheet for receiving, magnifying and projecting the projected image to the user's eyes.

5. The head-mounted fixing device as claimed in claim 4, wherein a second pivot is provided at pivoting connection between the arm assembly and at least one of the magnifying assembly and the reflection assembly.

6. The head-mounted fixing device as claimed in claim 4, wherein the reflection sheet is a convex mirror, and the magnifying sheet is a concave mirror.

7. The head-mounted fixing device as claimed in claim 1, wherein the top portion includes an elastic piece and a support strap, one end of the elastic piece is connected to the front frame portion, another end of the elastic piece is connected to one end of the support strap, and another end of the support strap is connected to the arc portion.

8. The head-mounted fixing device as claimed in claim 1, wherein the top portion includes an elastic piece, one end of the elastic piece is connected to the front frame portion, and another end of the elastic piece is connected to the arc portion.

9. The head-mounted fixing device as claimed in claim 7, wherein the elastic piece includes at least one stretchable structure.

10. The head-mounted fixing device as claimed in claim 7, wherein the another end of the elastic piece connected to the support strap is provided with a through hole, and the end of the support strap connected to the elastic piece is inserted through the through hole and then sticked to the support strap through a hook and loop fastener so that the support strap is connected to the elastic piece.

11. The head-mounted fixing device as claimed in claim 8, wherein one end of the elastic piece is provided with two through holes for the arc portion to pass through.

12. A head-mounted fixing device comprising:
a headgear configured to be worn on a user's head;
an arm assembly connected to the headgear and including a first pivot group and a second pivot group;
a reflection assembly mounted on the first pivot group and including a reflection sheet for reflecting a projected image, and the reflection sheet being a convex mirror; and
a magnifying assembly mounted on the second pivot group, wherein the reflection assembly is located between the magnifying assembly and the user's head, the magnifying assembly includes a magnifying sheet for receiving, magnifying and projecting the projected image to the user's eyes, and the magnifying sheet is a concave mirror.

13. The head-mounted fixing device as claimed in claim 12, wherein the headgear is provided with a hook and loop fastener and a ring-portion.

14. The head-mounted fixing device as claimed in claim 12, wherein the headgear includes an arc-shaped front frame portion, and two arc-shaped side frame portions connected to two ends of the front frame portion respectively.

15. The head-mounted fixing device as claimed in claim 12, wherein the headgear is provided with an engaging device.

16. A head-mounted fixing device comprising:
a head frame including two side frame portions, and a front frame portion located between the two side frame portions and connected to the two side frame portions, and the two side frame portions and the front frame portion being made of rigid materials;
a headgear including an arc portion and a top portion, wherein two ends of the arc portion are respectively connected to the two side frame portions, one end of the top portion is connected to the front frame portion, and another end of the top portion is connected to the arc portion;
an arm assembly connected to the head frame;
a reflection assembly mounted on the arm assembly and including a reflection sheet for reflecting a projected image; and
a magnifying assembly connected to the arm assembly so that the reflection assembly is located between the magnifying assembly and the user's head, and the magnifying assembly includes a magnifying sheet for receiving, magnifying and projecting the projected image to the user's eyes;
wherein the front frame portion is used to abut against a user's forehead to provide a fulcrum, the top portion supports the fulcrum, the arc portion is used to surround and abut against the back of the user's head, the reflection sheet is a convex mirror, and the magnifying sheet is a concave mirror.

* * * * *